(12) United States Patent
Crowe et al.

(10) Patent No.: US 7,257,448 B2
(45) Date of Patent: Aug. 14, 2007

(54) APPARATUS FOR STIMULATING A MUSCLE OF A SUBJECT

(75) Inventors: Louis Michael Crowe, Galway (IE); Brian Caulfield, Dublin (IE)

(73) Assignee: BMR Research & Development Limited, Galway (IE)

( * ) Notice: Subject to any disclaimer, the term of this patent is extended or adjusted under 35 U.S.C. 154(b) by 172 days.

(21) Appl. No.: 10/047,383

(22) Filed: Jan. 14, 2002

(65) Prior Publication Data

US 2002/0165590 A1 Nov. 7, 2002

(30) Foreign Application Priority Data

Jan. 16, 2001 (IE) .............................. s2001/0032

(51) Int. Cl.
*A61N 1/36* (2006.01)
(52) U.S. Cl. ..................................... 607/62; 607/48
(58) Field of Classification Search ................ 607/72, 607/62, 46, 48, 49
See application file for complete search history.

(56) References Cited

U.S. PATENT DOCUMENTS

| | | | |
|---|---|---|---|
| 4,392,496 A | | 7/1983 | Stanton |
| 4,642,769 A | * | 2/1987 | Petrofsky ..................... 607/48 |
| 4,712,558 A | | 12/1987 | Kidd et al. |
| 4,785,813 A | | 11/1988 | Petrofsky |
| 4,838,272 A | | 6/1989 | Lieber |
| 4,976,264 A | | 12/1990 | Petrofsky |
| 5,048,522 A | | 9/1991 | Petrofsky |
| 5,070,873 A | | 12/1991 | Graupe et al. |
| 5,285,781 A | | 2/1994 | Brodard |
| 5,344,386 A | | 9/1994 | Schaldach |
| 5,507,788 A | * | 4/1996 | Lieber ......................... 607/48 |
| 5,549,656 A | * | 8/1996 | Reiss ........................... 607/48 |
| 5,562,707 A | | 10/1996 | Prochazka et al. |
| 5,628,722 A | | 5/1997 | Solomonow et al. |
| RE36,690 E | | 5/2000 | McGraw et al. |
| 6,064,911 A | | 5/2000 | Wingrove |
| 6,236,890 B1 | | 5/2001 | Oldham |
| 6,324,432 B1 | | 11/2001 | Rigaux et al. |

(Continued)

FOREIGN PATENT DOCUMENTS

EP 0 483 072 4/1992

(Continued)

OTHER PUBLICATIONS

The Facts About Weight Loss Products and Programs; presented as a Public Service by: Federal Trade Commission, Food and Drug Administration, National Association of Attorneys General, FDA/FTC/NAAG Brochure: 1992; pp. 1 to 6.

*Primary Examiner*—George R. Evanisko
(74) *Attorney, Agent, or Firm*—Drinker Biddle & Reath LLP

(57) ABSTRACT

A method and apparatus for stimulating a muscle of a subject are provided. The apparatus comprises a signal generator for generating an electrical pulse signal of a frequency and a current amplitude for inducing contractions in the muscle, and an electrode apparatus for applying the signal to nerves associated with the muscle to be stimulated or adjacent the muscle of the subject for stimulating the muscle. The frequency and current amplitude of the electrical pulse signal are selected so as to maximize the bulk of the muscle being subjected to the contractions so as to generate a shivering phenomenon therein.

32 Claims, 7 Drawing Sheets

U.S. PATENT DOCUMENTS 6,701,190 B2 * 3/2004 Gliner .................. 607/62

FOREIGN PATENT DOCUMENTS

| GB | 2 261 377 | 5/1993 |
| GB | 2 359 758 | 9/2001 |
| WO | WO97/47357 | 12/1997 |
| WO | WO 00/41764 * | 7/2000 |
| WO | WO 02/22205 | 3/2002 |

* cited by examiner

| 1 PORT | TIME1 | TIME2 | TIME3 | TIME4 |
|---|---|---|---|---|
| A | HI | HI | HI | HI |
| B | LO | LO | LO | X |
| C | X | X | HI | X |
| D | HI | X | X | LO |
| TIME | 100 | 100 | 300 | 125 |

| 2 PORT | TIME1 | TIME2 | TIME3 | TIME4 |
|---|---|---|---|---|
| A | HI | HI | HI | HI |
| B | X | LO | LO | X |
| C | X | X | HI | X |
| D | LO | X | X | LO |
| TIME | 100 | 100 | 300 | 125 |

| 3 PORT | TIME1 | TIME2 | TIME3 | TIME4 |
|---|---|---|---|---|
| A | HI | HI | HI | HI |
| B | X | LO | LO | X |
| C | X | X | HI | X |
| D | LO | X | X | LO |
| TIME | 50 | 100 | 350 | 125 |

| 4 PORT | TIME1 | TIME2 | TIME3 | TIME4 |
|---|---|---|---|---|
| A | X | HI | HI | HI |
| B | HI | LO | LO | X |
| C | LO | X | HI | X |
| D | X | X | X | LO |
| TIME | 100 | 200 | 225 | 100 |

| 5 PORT | TIME1 | TIME2 | TIME3 | TIME4 |
|---|---|---|---|---|
| A | X | HI | HI | HI |
| B | HI | LO | LO | X |
| C | LO | X | HI | X |
| D | X | X | X | LO |
| TIME | 75 | 200 | 275 | 75 |

| 6 PORT | TIME1 | TIME2 | TIME3 | TIME4 |
|---|---|---|---|---|
| A | LO | X | HI | HI |
| B | HI | HI | LO | X |
| C | X | LO | HI | X |
| D | HI | X | X | LO |
| TIME | 250 | 50 | 250 | 100 |

| 7 PORT | TIME1 | TIME2 | TIME3 | TIME4 |
|---|---|---|---|---|
| A | X | HI | HI | HI |
| B | HI | LO | LO | X |
| C | LO | X | HI | X |
| D | X | X | X | 1 |
| TIME | 75 | 200 | 275 | 150 |

| 8 PORT | TIME1 | TIME2 | TIME3 | TIME4 |
|---|---|---|---|---|
| A | HI | HI | HI | HI |
| B | X | LO | LO | X |
| C | X | X | HI | X |
| D | LO | X | X | LO |
| TIME | 50 | 100 | 300 | 125 |

| 9 PORT | TIME1 | TIME2 | TIME3 | TIME4 |
|---|---|---|---|---|
| A | HI | HI | HI | X |
| B | LO | LO | LO | LO |
| C | X | X | HI | HI |
| D | X | X | X | X |
| TIME | 150 | 150 | 150 | 100 |

*Fig. 6*

APPARATUS FOR STIMULATING A MUSCLE OF A SUBJECT

BACKGROUND OF THE INVENTION

The present invention relates to apparatus for stimulating a muscle of a subject, and in particular, to such apparatus for inducing cardiovascular training effects in a subject and for inducing relatively significant calorie usage that may bring about weight loss in the subject over time. The invention also relates to a method for stimulating a muscle in a subject for inducing cardiovascular training effects in a subject, and for inducing relatively significant calorie usage that may bring about weight loss in the subject. As a subject's weight change is a function of caloric intake as compared with caloric expenditure over time, the invention allows for a significant increase in caloric expenditure.

SUMMARY OF THE INVENTION

According to the invention there is provided apparatus and method for stimulating a muscle of a subject for inducing cardiovascular training effects in a subject, and for inducing relatively significant calorie usage that may bring about weight loss in the subject. As a subject's weight change is a function of caloric intake as compared with caloric expenditure over time, the invention allows for a significant increase in caloric expenditure.

In the past it has generally been believed that muscle stimulation by electrical pulse signals was ineffective for inducing cardiovascular training effects in a subject, and for inducing relatively significant calorie usage to bring about weight loss in the subject. However, in accordance with the invention it has been determined by the inventors that the method and apparatus according to the present invention is particularly effective for inducing cardiovascular training effects in a subject, and for inducing relatively significant calorie usage which may bring about weight loss in the subject.

The body has evolved into a very energy efficient machine. Being able to perform a greater amount of activity for a given intake of food has conferred obvious survival benefits. The exception to this rule is where there is a danger of hypothermia, (cold). Here the body has evolved a defense mechanism to generate heat, i.e. burn calories, without doing any external work. Internal actions of the body generate heat to counteract the dangers associated with hypothermia. There are two principle mechanisms utilized by the body to generate this heat. As has been determined by the inventors of the present invention, these mechanisms include shivering and the utilization of 'brown fat'. In an adult shivering is the mechanism of greatest importance. Shivering produces large amounts of heat without performing any external work, i.e. a subject does not have to lift boxes up a hill, etc. Therefore, the inventors of the present invention have determined that if shivering-type movements of large amounts of muscle bulk can be induced with electrical stimulation, this shivering would be the best way to consume large amounts of energy without performing any external work.

This shivering phenomenon is preferably induced according to the embodiments of the invention described below employing externally placed electrode pads. However, the shivering phenomenon may also be produced using any standard nerve stimulation techniques. These may include the use of having fully implanted electrodes and/or dermal/subdermal electrodes. The implementation of the invention employing these alternative electrode designs will also employ differing electrode placements, size, as well as different currents, etc. Different types of stimulators, for instance stimulators based on magnetic fields or interferential stimulators, or based on other technologies that are able to stimulate the nerves and/or muscles of a subject are contemplated to be part of the invention.

Shivering induced in accordance with the invention comprises any substantial involuntary muscle movement that is repeated over a predetermined time period for the purpose of expending calories. This shivering may be continuous or may allow for intermittent periods of rest or of lesser shivering intensity.

This shivering also encompasses all such muscle movements, irrespective of frequency or intensity, as long as designed to burn calories in a subject.

An electrical stimulation device that works the muscles very hard has obvious appeal. For instance, such a device could burn significant amounts of calories and bring about cardiovascular training effects both in healthy and unhealthy people. Indeed, to boost product sales of various prior devices, such claims are regularly made, and indeed have been made for decades. However, in the past these have been fraudulent according to leading authorities such as the Food and Drugs Authority in the United States. Indeed, the FDA's official website indicates that they have taken a number of electrical muscle stimulators off the market as phony devices because they were promoted for weight loss and body toning.

All electrical stimulation must burn some calories, otherwise it could not move muscle. However, the problem is that with the stimulation methods and programs used to date, significant calories were not burned unless other exercise is used in conjunction with the electrical stimulation. Significant may be defined in several ways. In accordance with the invention, it is defined that the energy usage attainable must be of sufficient intensity that it brings about a cardiovascular training effect in normal subjects, (generally this needs to be above 50% of maximum cardiac output, and preferentially 60% or 70%.).

The present invention overcomes this problem. A method and apparatus have been invented whereby significant amounts of energy are expended and calories are burned. In accordance with the invention, maximum cardiac output may be achieved, even in young healthy individuals. For instance, while using the invention, the inventor's heart rate has increased to 200 beats per minute during training sessions, consuming 15 kcal/min/kg, the equivalent of running. Naturally, this vigorous cardiovascular exercise brings about very significant training effects. With hardly any voluntary exercise the inventor was able to run a marathon after only a couple of months training with the invention. Ordinary people using the stimulation at tolerable levels in accordance with the invention may achieve significant energy utilization rates. Ten members of the research team used this technique for an average of 24 sessions. Their fitness rankings, according to the Queen's College step test, increased by an average of 18% points. On average they were able to exercise using this method at energy consumption levels equivalent to swimming. A complete discussion of these subjects will be made below.

The apparatus in accordance with the invention comprises a signal generator for generating an electrical pulse signal and an electrode apparatus for applying the signal to nerves associated with the muscle to be stimulated or adjacent the muscle of the subject for stimulating the muscle. The signal generator generates the pulse signal having various predefined parameters for inducing contractions in the muscle at a frequency in the range of 3 Hz to 12 Hz and preferably at a frequency of 4 Hz to 8 Hz. Advantageously, the predefined parameters of the pulse signal are selected so as to maximize the bulk of the muscle being subjected to the contractions and to control the intensity of these contractions. These contractions are designed to generate a shivering phenomenon, as noted above, to generate work in the muscles of the subject without performing any external work by the subject. A cardiovascular response is generated in response to this generated shivering phenomenon, as will be defined below.

In one embodiment of the invention the pulse signal generated by the signal generator is defined by appropriate predetermined parameters for minimising discomfort to the subject. It is well known that the application of a relative high intensity electrical pulse to a subject may result in a discomfort to the subject. The typical response to this discomfort has been to provide various devices using a very low intensity pulse for a short application period. However, it is just these parameters and short periods that result in an ineffective product.

The present invention allows for pulses having sufficient intensity and appropriate other parameters to burn a substantial amount of calories without discomfort to the subject.

It has been determined by the inventors that to maximize the level of energy dissipation in the target muscles it is necessary to recruit as many muscle motor units as possible into the shivering action. (A motor unit comprises a motor neuron and all the muscle fibers which it innervates). In electrical stimulation, a given motor unit fires only if the externally applied electrical stimulus in its immediate neighborhood exceeds its stimulation threshold.

External stimulation of a nerve, e.g., a motor neuron, occurs if the electrical potential across its membrane is reduced from its resting level of about −70 mV to its trigger level of about −50 mV. However, to alter the potential in this way involves the transfer of an amount of electrical charge, since the membrane itself has electrical capacitance, and moreover there are local membrane currents also affecting the potential. This means that the local condition for stimulation is that an externally applied current density of a sufficient level is sustained for a sufficient time to cause the membrane potential to reduce to the trigger level. The current density level and time required depends on the type of fiber with larger diameter motor neurons having lower stimulation thresholds than smaller diameter ones.

In reality there are thousands of nerves supplying muscle which are proximally arranged in bundles which are branched out more distally throughout the target tissue. For each of these to fire it is necessary to meet the local stimulation conditions. Some nerves are easier to reach from the level of the skin and therefore will be more readily stimulated. Some nerves will be favored by their orientation while others will be shielded by other structures. So for given skin electrode sizes and positions on an individual subject, it is possible to think of a probability distribution defined throughout the neural network, giving the probability of stimulation at each point as a function of the current applied to the skin electrodes.

Using a relatively large charge per pulse would normally be painful if applied through standard skin electrodes. This is because the current density would be relatively high and therefore risk stimulating pain receptors. In order to utilise the larger current required in this application it is therefore necessary to use large electrodes which minimise the current density at the skin. The larger electrodes have the further advantage of distributing the current in the subcutaneous tissue more widely, thereby increasing the probability of recruiting more nerves and hence muscle fibers.

In accordance with the invention, the pulse signal may comprise a plurality of single pulses at a frequency for inducing the contractions in the muscle of the subject within the frequency range of 3 Hz to 12 Hz, or may comprise a plurality of bursts of pulses, the frequency of the respective bursts of pulses being such as to induce contractions in the muscle of the subject within the frequency range of 3 Hz to 12 Hz, and the current amplitude and frequency of the pulses within each burst of pulses being such as to avoid contractions of the muscle at frequencies above 12 Hz. It should be noted that the main muscle bulk vibrates/shakes/shivers within this frequency range. It should also be noted that the muscle may be set to vibrate at a frequency of, say, 15, encompassing, say, 5 large contractions and interspersed with 10 lesser ones that may or may not build up to the stronger contractions. It should also be noted that the frequency of the pulses sent out is not what determines the functioning of the method but rather the frequency of the muscle contractions. For instance, there may be a background pulse frequency of 100 $H_z$ used to stimulate the skin touch fibers but having little effect on the muscle itself. It is contemplated that these variations are within the scope of the invention.

Preferably, the charge per pulse of the pulses of the pulse signal are approximately in the range of 0 to 120 µC (micro-coulombs) for pulse durations of a length employed by the examples set forth below, e.g., approximately 300-700 µsec. While pulse length/charge combinations outside of these ranges are contemplated by the invention, different corresponding charges per pulse for these different pulse lengths would also be employed. The means for applying the pulse signal to the subject co-operate with each other to avoid the charge per pulse per unit area exceeding 16 $nC/mm^2$ in the subject adjacent the means for applying the pulse signal to the subject. In one embodiment of the invention the charge per pulse per unit area in the subject adjacent the means for applying the pulse signal to the subject does not exceed 8 $nC/mm^2$.

Preferably, the peak current amplitude of the pulses of the pulse signal, and the means for applying the pulse signal to the subject co-operate with each other to avoid the peak current density exceeding 0.027 $mA/mm^2$ in the subject adjacent the means for applying the pulse signal to the subject. In one embodiment of the invention the current density in the subject adjacent the means for applying the pulse signal to the subject does not exceed 0.14$m/A/mm^2$.

In one embodiment of the invention the maximum current amplitude of the pulse signal does not exceed 200 mA and preferably, the maximum current amplitude of the pulse signal lies in the range of 80 mA to 200 mA, and advantageously in the range 100 mA to 200 mA.

In one embodiment of the invention at least one of the electrode pads is of effective electrical contact area such that the length of the effective electrical contact area is substantially similar to the width of the muscle/muscle group to be stimulated.

In an embodiment of the invention where it is desired to stimulate a quadriceps or hamstring muscle group in a male of average size, it is preferred that the length of the effect of electrical contact area of the relevant electrode pad should be at least 140 mm, and preferably, at least 190 mm.

In another embodiment of the invention when the pulse signal comprises a plurality of single pulses the frequency of the respective pulses lies in the range 3 Hz to 12 Hz, and preferably, in the range 4 Hz to 8 Hz. Advantageously, when the pulse signal comprises a plurality of bursts of pulses, the frequency of the bursts lie in the range of 3 Hz to 12 Hz, and preferably, in the range 4 Hz to 8 Hz. Preferably, the frequency of the pulses within each burst of pulses should be greater than 20 Hz. In one embodiment of the invention the current amplitude of the respective pulses within each burst are within an envelope which defines a curve which rises from a first lower current amplitude value to a peak current amplitude value, and then returns to a second lower amplitude value. In another embodiment of the invention where each burst of pulses comprises two or more pulses, the respective pulses in the burst of pulses may be of similar or different current amplitude values. Preferably, this embodiment employs a pulse at the peak current amplitude value and another pulse, either before or after its peak pulse, are within the amplitude envelope. In another embodiment of the invention, the amplitude value or charge of the pulse adjacent the peak pulse do not exceed more than 60% of the peak pulse's amplitude value or charge. In another embodiment of the invention the first and second lower current amplitude values are similar. In another embodiment of the invention two adjacent pulse signals of each burst of pulse signals adjacent to the peak amplitude value of the envelope are of similar current amplitude value.

To facilitate an understanding of the invention a non-limiting example of apparatus according to the invention will be described, and examples of use of the invention in inducing cardiovascular training effects in a subject, and in inducing relatively significant calorie usage to bring about weight loss in the subject will then be described.

Still other objects and advantages of the invention will in part be obvious and will in part be apparent from the specification and the drawings.

The invention accordingly comprises the several steps and the relation of one or more of such steps with respect to each of the others, and the apparatus embodying features of construction, combinations of elements and arrangements of parts that are adapted to effect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which:

FIG. 6 depicts various stimulation pulse sequences in accordance with the invention.

DETAILED DESCRIPTION OF THE PREFERRED EMBODIMENTS

Figure 1:
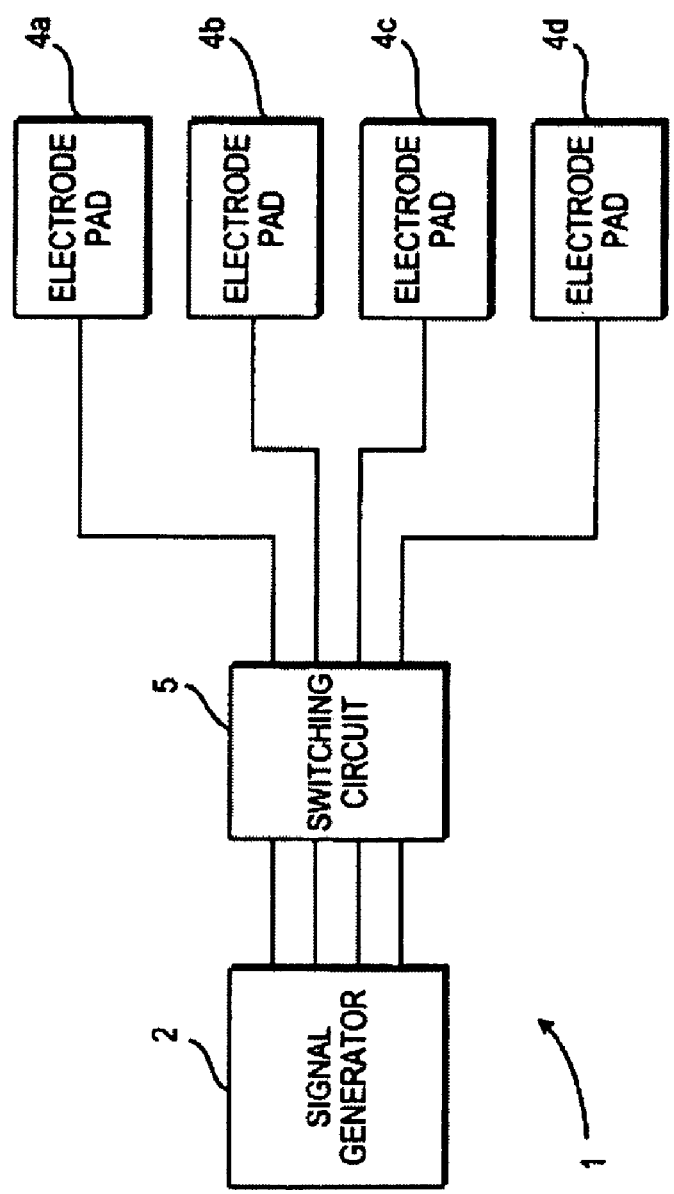
FIG. 1 is a block diagram depicting an apparatus constructed in accordance with the invention for stimulating a muscle of a subject to generate a shivering phenomenon for inducing cardiovascular training effects in a subject, and for inducing relatively significant calorie usage which may bring about weight loss in the subject.

In accordance with the invention, it has been determined by the inventors that in order to induce a relatively significant calorie usage through electrical stimulation of the muscles of a subject that may bring about weight loss in the subject, the energy usage by stimulating the muscles must be of sufficient intensity that it brings about a cardiovascular training effect in the subject. It has further been determined that the energy usage should be at least 50% and preferably above 60% to 70% of the maximum cardiac output of the subject. This can best be achieved by ensuring that the maximum muscle bulk possible is stimulated and that it is stimulated at the optimal rate, while at the same time avoiding discomfort to the subject.

It has been determined by the inventors of the invention that the body is capable of generating internal heat by shivering. Shivering is caused by rapid muscle contractions without gross movement of the limbs. In general, one would assume that the greater the rate of muscle contractions during shivering, the greater the amount of heat generated. However, the inventors of the invention have determined that this is not the case. Indeed, it has been determined that muscle contractions during natural shivering remain relatively constant between 3 Hz to 8 Hz irrespective of the temperature of the body. Therefore, increasing heat output and muscle usage is not affected by the rate of shivering.

Therefore, in accordance with the invention, it is has been determined that in order to increase the heat generating capacity of the muscles during shivering the muscle bulk which is subjected to shivering must be maximized. It has further been determined that for a given muscle there is an optimal rate of contraction and relaxation that produces the optimal amount of energy with little or no external work. It has been determine that this rate lies within the frequency range of 4 Hz to 8 Hz. Furthermore, it has also been determined that within an individual muscle, contractions between various muscle fibers are almost synchronous. During a normal movement, only a certain percentage of the muscle fibers perform work to contract the muscle. It is postulated that, in accordance with the invention, more of these muscle fibers, when electrically stimulated, contract in parallel, thereby using additional energy but producing little additional external work.

Accordingly, in view of the fact that muscles contract at a rate of between approximately 4 Hz and 8 Hz during natural shivering, it has been determined that stimulating the muscles at this rate similarly causes very high energy usage by the muscles, thus, leading to the burning of calories and potential weight loss. It has also been determined that causing the muscles to contract at a rate below 3 Hz or above 12 Hz results in diminishing energy utilization by the muscles. Thus, in order to cause the muscles to contract at a frequency in the range of 4 Hz to 8 Hz the pulse train should preferably be selected to produce a single pulse or a burst of pulses at a frequency of 4 Hz to 8 Hz or a series of pulses or bursts of pulses that undulate in intensity around this frequency. While a single pulse at a frequency of 4 Hz has been determined to provide good stimulation of the muscles at the desired 4 Hz to 8 Hz contraction rate, it has been further determined that bursts of pulses at 4 Hz to 8 Hz where each burst comprises two pulses provide a significantly increased energy utilization by the muscles. The details of the application of such pulse trains will be described below after description of the overall design of the apparatus and method of the invention.

Referring next to FIG. 1, there is illustrated apparatus according to the invention indicated generally by the reference numeral 1 for stimulating muscles of a subject for inducing cardiovascular training effects in the subject, and for inducing relatively significant calorie usage which may bring about weight loss in the subject. As is noted above, while the described apparatus is preferably utilized for inducing the shivering phenomenon, any apparatus for sufficiently inducing such muscle contractions, as noted above, may be employed. Apparatus 1 comprises a signal generator 2 for generating a square wave or other appropriate electrical pulse signal (biphasic, symmetrical and flipping polarity with each pulse/burst of pulses) for applying to a subject through two or more electrode pads for stimulating one or more muscles of the subject. In this particular case two sets of four electrode pads 4a, 4b, 4c and 4d are provided, one set for each leg, for stimulating the hamstring, the quadriceps, the glutei and the muscles above the knee, respectively. A switching circuit 5 permits the pulse signals from signal generator 2 to be selectively applied to electrode pads 4a-4d. Signal generator 2 is a variable frequency and variable current amplitude generator and is suitable for generating pulse signals at selectable frequencies, and of selectable constant current amplitudes as well as selectable varying current amplitudes. Typically, signal generator 2 is capable of generating trains of pulse signals of frequency up to 200 Hz and current amplitude up to 200 mA. 200 mA is a much greater output than is normal in the marketplace for such pulse generators.

Figure 2A:
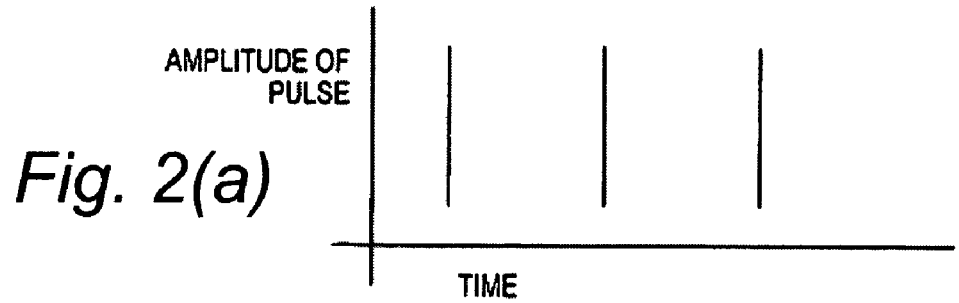
FIGS. 2(a) to (c) are graphical representations of pulse signals that may be produced by the apparatus of FIG. 1 in accordance with the invention.
Figure 2B:
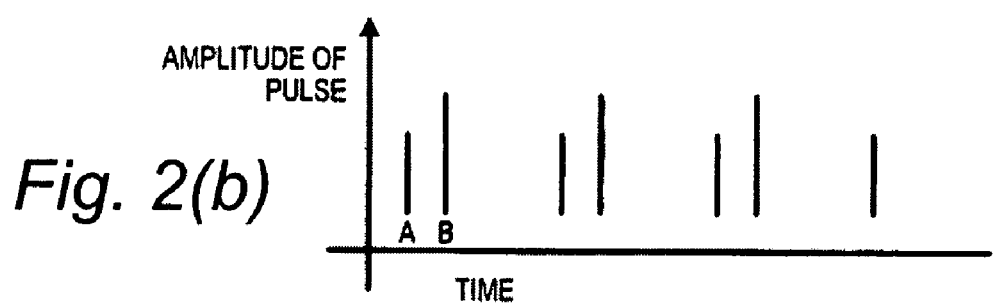
Figure 2C:
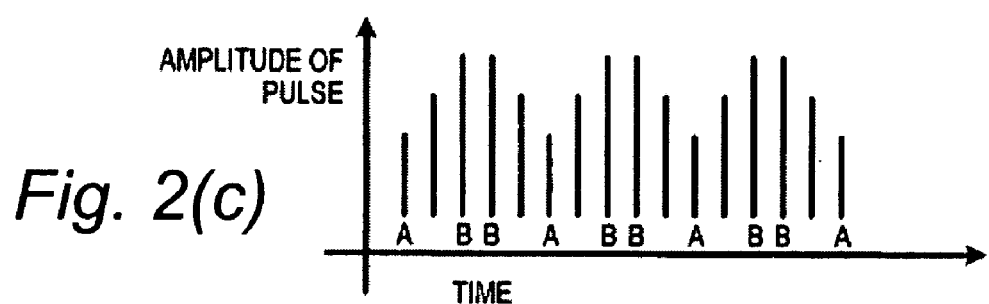

Referring next to FIGS. 2(a) to (c) typical pulse trains which may be generated by the signal generator 2 are illustrated. FIG. 2(a) illustrates the simplest form of pulse signal where the current amplitude is selectable by the user and the frequency is also maintained constant. As noted above, it has been determined in accordance with the invention that when this pulse train is selected the ideal frequency preferably lies in the range of 4 Hz to 8 Hz, and the total charge is selected by the user at a maximum comfortable value. This is preferentially between about 60-120 $\mu$C (microcoulombs). By selecting the frequency of the pulses to be in the range of 4 Hz to 8 Hz, the frequency of contractions induced in the selected muscles is similar to the pulse frequency. The current amplitude is selected to generate an appropriate current to avoid discomfort to the subject.

As noted above, it is the effective muscle contraction frequency which is preferably in the range of 4 Hz to 8 Hz. This muscle contraction rate may be achieved with other pulse sequences. Thus, the frequency of the pulses sent out is not what determines the functioning of the method but rather the frequency of the muscle contractions. For instance, there may be a background pulse frequency of 100 Hz used to stimulate the skin touch fibers but having little effect on the muscle itself. It is contemplated that these variations are within the scope of the invention.

FIG. 2(b) illustrates a pulse signal comprising bursts of pulse signals, each burst comprising two signals of differing intensities having a fixed relationship with respect to each other. The overall intensity of the burst is selectable by the user. When this train of pulse signals is used the frequency of the bursts preferably lies in the range of 4 Hz to 8 Hz while the frequency of the pulses within each burst are preferably greater than 20 Hz. The current amplitude (or charge) of the first pulse A in each burst preferably lies in the range of approximately 50%-60% of the current amplitude (or charge) of the second pulse of each burst, and the second pulse B of each burst preferably has a charge of between approximately 60-120 $\mu$C but other values that may be tolerated by a subject, either higher or lower than this range may be employed. Of course, the pulses could be reversed with the second being approximately 50%-60% of the first.

The ideal pulse train is that illustrated in FIG. 2(b) has been determined to generate the least discomfort to a user. Each burst comprises two pulses at a frequency of 25 Hz whereby the first pulse is preferably of a current amplitude of approximately half that of the current amplitude of the second pulse. The frequency of the bursts is preferably between 4 Hz and 8 Hz as desired. While the provision of a third pulse in each pulse burst may further increase energy usage by the muscles, the stimulation becomes less comfortable for the subject because the contractions may begin to become tetanic. This, thus, prevents the subject from increasing the amplitude of the signal, and in turn the current density in the subject adjacent to the electrode pads in order to increase the muscle bulk which is being stimulated.

As discussed above it is important to maximize the muscle bulk that is stimulated, and this is achieved by maximizing the charge per pulse of the signal. Additionally, by ensuring relatively large effective electrical contact area of the electrode pads the higher current amplitude signals may be tolerated, without increasing the current density in the subject adjacent to the electrode pads. By using the pulse train illustrated in FIG. 2(b), for example, it has been determined that the first pulse of lower amplitude of each burst causes some of the targeted muscles to be stimulated, while the second pulse of higher amplitude causes the remainder of the targeted muscles to be stimulated. However, the second pulse in each burst does not induce an additional contraction in the muscles which have commenced contraction as a result of the first of the two pulses, rather, the second pulse merely continues the contraction commenced by the first pulse. This is due to the fact that the frequency of the pulses of each burst is of frequency not less than 20 Hz. By providing the first pulse in each burst as being the lower amplitude pulse significantly less discomfort is caused to the subject for a given value of current amplitudes for the two pulses.

A pulse train illustrated in FIG. 2(c) is of selectable constant frequency and selectable varying constant current amplitude (charge). The pulse train comprises a plurality of bursts of pulse signals, the frequency of each burst of pulse signals preferably being in the range of 4 Hz to 8 Hz. Each burst of pulse signals comprises six pulses which form an envelope commencing with a first lower current amplitude pulse raising to two adjacent similar peak current amplitude pulses B and then falling to a lower second current amplitude pulse A. The first and second lower current amplitude pulses A are of similar current which is preferably approximately 50% of the current amplitude of the peak pulses B. The charge emitted by the two adjacent peak pulses B is preferably in the range of 60-120 $\mu$C. The frequency of the pulses within each burst of pulses is preferably constant and greater than 20 Hz, and may be as high as 200 Hz.

The pulse train of FIG. 2(c) has also been determined to be effective, and minimises discomfort to the subject. However, it is important that the frequency of the pulses within each burst should not fall below 20 Hz, otherwise, they would tend to act as individual pulses. Thus, each pulse would cause a contraction which would thus cause the muscles to contract at the frequency of the pulses in the pulse signal. Each pulse within the bursts of pulses may therefore stimulate an independent, separate muscle contraction, rather than comprise a group of pulses within each burst working together to generate a single contraction.

The effective electrical contact area of each electrode pad 4a-4d (see FIG. 1) which is brought into contact with the skin of the subject should be such as to ensure that the current provided to the subject adjacent to the electrode pad does not exceed a stimulation threshold of the pain fibers of the subject. In order to achieve this goal it is necessary to determine the area of the electrode pads in conjunction with the maximum current amplitude or charge per pulse, of the pulse train to be applied to the subject. In order to provide maximum current at the lowest current density the largest possible electrode should be used. However, this will result in a substantial portion of the charge not being directed to the desired muscle group, and therefore the system becomes less energy efficient. Therefore, the largest electrode that still allows substantially all of the current to be directed to the desired muscle group should be employed. Preferably with a pulse train of charge per pulse of 120 µC, the electrode pads 4a-4b, for example, should have an effective electrical contact area preferably on the order of 200 cm$^2$ or greater. Preferably, pads 4a-4b should be rectangular and of dimensions 20 cm by 10 cm. This large size is employable because of the application of the various pulse trains of the invention. The size of others of the electrodes are selected similarly, and also to provide desired current distributions of multiple current paths that are employed.

As noted above, it has been determined by the inventors that to maximize the level of energy dissipation in the target muscles it is necessary to recruit as many muscle motor units as possible into the shivering action. (A motor unit comprises a motor neuron and all the muscle fibers which it innervates). In electrical stimulation, a given motor unit fires only if the externally applied electrical stimulus in its immediate neighborhood exceeds its stimulation threshold.

External stimulation of a nerve, e.g., motor neuron, occurs if the electrical potential across its membrane is reduced from its resting level of about −70 mV to its trigger level of about −50 mV. However, to alter the potential in this way involves the transfer of an amount of electrical charge, since the membrane itself has electrical capacitance, and moreover there are local membrane currents also affecting the potential. This means that the local condition for stimulation is that an externally applied current density of a sufficient level is sustained for a sufficient time to cause the membrane potential to reduce to the trigger level. The current density level and time required depends on the type of fiber with larger diameter motor neurons having lower stimulation thresholds than smaller diameter ones.

In reality there are thousands of nerves supplying muscle which are proximally arranged in bundles which are branched out more distally throughout the target tissue. For each of these to fire it is necessary to meet the local stimulation conditions. Some nerves are easier to reach from the level of the skin and therefore will be more readily stimulated. Some nerves will be favored by their orientation while others will be shielded by other structures. So for given skin electrode sizes and positions on an individual subject, it is possible to think of a probability distribution defined throughout the neural network, giving the probability of stimulation at each point as a function of the current applied to the skin electrodes. In practical terms, we have determined that to maximize the number of motor units recruited to the shivering action in the muscles of the leg, using skin electrodes, it is preferable to use peak currents in the order of 200 mA, sustained for pulse durations in the order of 600 µsec and directed to pass through the bulk of the muscle. Such a pulse has a charge content of 120 µC (micro-coulombs) and is quite large by standards of most clinical stimulators whose pulse outputs are normally restricted to 30 µC.

For a rectangular shaped current pulse, the maximum required charge per pulse in the region of 120 µC could be achieved by many different combinations of pulse amplitude and pulse width. Various pulse shapes could also be used, for example triangular or exponential, provided the integral of current with time during the pulse yields a charge level in the order of 120 µC.

This relatively large charge per pulse would normally be painful if applied through standard skin electrodes which are typically in the order 5 to 20 cm$^2$. This is because the current density would be relatively high and therefore risk stimulating pain receptors. In order to utilise the larger current required in this application it is therefore necessary to use large electrodes which minimise the current density at the skin. The larger electrodes have the further advantage of distributing the current in the subcutaneous tissue more widely, thereby increasing the probability of recruiting nerve supplying muscle.

Figures 3A, 3B:
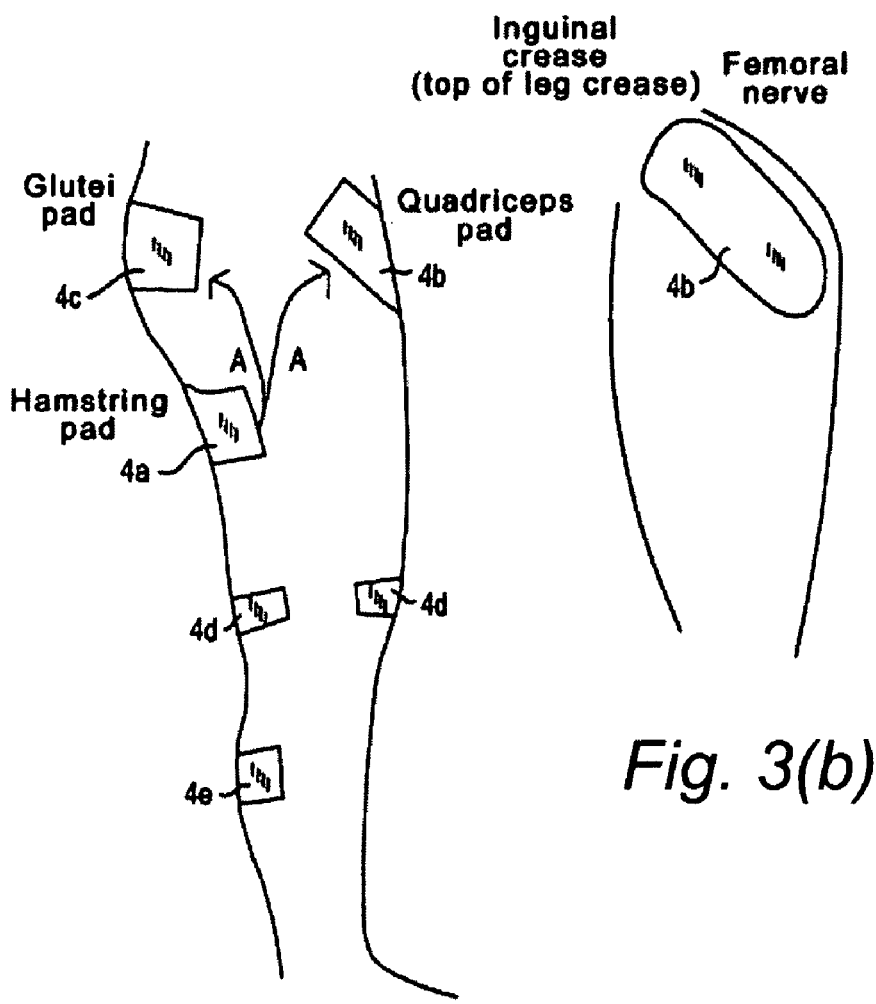
FIGS. 3(a) and 3(b) are diagrammatic representations of use of the apparatus of FIG. 1 in accordance with the invention.

Referring next to FIGS. 3a and 3b, electrodes 4a-4d are placed on the respective muscle groups. In accordance with a preferred embodiment of the invention, electrode pads 4a are placed on the hamstring muscle groups of the respective legs, electrode pads 4b are placed on the quadriceps muscle groups, electrode pads 4c are placed on the glutei muscle groups, while electrode pads 4d are placed above the knee on the front and rear of the respective legs. Each electrode pad 4d comprises two parts that act electrically as a single electrode. This electrode 4d is most beneficial at lower intensities. At higher intensities, the current from the other electrodes is sufficient to work the muscles above the knee. Pulses with any of the selected parameters described above (see FIGS. 2a-2c) are applied to the subject through electrode pads 4a to 4d.

The direction in which current is applied through electrode pads 4a-4d to the subject is selectable in accordance with settings of switching circuit 5. One method for applying the pulse signals to the subject is to select electrode pads 4a-4d in pairs, one pad on each leg. Thus, one pair may comprise the electrode pads 4a on the respective legs of the subject. The other pair may comprise the electrode pads 4b, 4c, and 4d on the respective legs of the subject. The pulse signal is thus applied to the respective hamstring muscle groups through the pair of electrode pads 4a, the pulse signal is applied to the quadriceps muscle groups through the pair of electrode pads 4b while the pulse signal is applied to the glutei muscle groups through the pair of electrode pads 4c and similarly the electrode pulses are applied to the muscles above the knee through the pair of electrode pads 4d. In each case, one pad of the selected pair of electrode pads acts as an anode while the other acts as a cathode for the initial phase of a pulse. The function of each electrode pad may be switched during operation, from anode to cathode, as specified by switching circuit 5. Of course, each electrode may be designed to include both an anode and a cathode. The pulse signals for the respective muscle groups may be the same or different.

An alternative method for applying the pulse signals to the subject is to select pairs of electrode pairs on a single leg. For example, the pulse signal may be applied to the hamstring and quadriceps muscle groups on each leg through hamstring pad 4a and quadriceps pad 4b on the corresponding leg.

A further alternative method for applying the pulse signal to the subject is to select a combination of electrodes on a single leg. For example, hamstring pad 4a may be placed on the femur of each leg relative to the quadriceps pad and glutei pad 4b and 4c so that current passing through the subject from hamstring pad 4a passes in the directions of the arrows A of FIG. 3(a) and passes out of the subject through quadriceps and glutei pads 4b and 4c, respectively. Electrode pads 4a, 4b and 4c can then be arranged so that the current passes through the nerves that activate the hamstring, quadriceps and glutei muscles for in turn stimulating these muscles in the respective legs.

It has also been determined that in order to improve the level of comfort of the subject, as well as for convenience and electrical efficiency, the calf muscles of the leg of the subject need not be stimulated by placing electrode pads directly over the calf muscle group, but rather by passing the pulse signals through the sciatic nerve above the knee. This can be achieved by passing pulse signals from hamstring electrode 4a to quadriceps electrode 4b and glutei electrode 4c simultaneously as illustrated by arrows A in FIG. 3(a).

In a still further alternative embodiment of the invention, a calf pad 4e may be employed, thereby providing direct stimulation of the calf muscle.

Therefore, any combinations of electrodes may be employed. The preferred combinations of the invention include using the same one or more electrodes on different legs, using different electrodes on the same leg, and using a combination of electrodes on the same leg.

Preferably, in accordance with preferred embodiments of the present invention discrete pulses of electrical energy with each pulse persisting continuously throughout a number of contiguous time periods (also referred to herein as time slots) are used. An array (greater than two) of electrodes are selectively activated during the occurrence of the pulse to produce a pattern of electrical activity between them. Different combinations of electrode pairs are used during each time slot to produce a greater number of potential stimulation therapies than the number of electrodes.

A table depicting various stimulator pulse sequences is shown in FIG. 6. In each time slot the stimulation current goes 'from' one or more electrodes (A, B, C, D) 'to' one or more other electrodes (A, B, C, D). These electrodes preferably correspond to electrodes 4a, 4b, 4c and 4d of FIGS. 3(a) and 3(b), respectively. The electrode(s) the current is coming from (anode) are designated HIGH (hi). The electrode(s) the current is going to (cathode) is/are designated LOW (lo) or SINK. An electrode that is not active is designated OFF (x). Each electrode can be selectively switched on-high (hi), on-low/sink (lo) or off (X) in any combination in each time slot. A length of each time slot is also indicated. The time slots follow consecutively with the switching of the electrodes taking place at the break between consecutive time slots. Furthermore, each table of FIG. 6 preferably describes one half of a stimulation. Thus, in order to insure a net zero current buildup, after each current pulse sequence designated by each table, the inverse sequence of that shown in the table is applied. An interphase delay may be interposed between these two sequences.

In accordance with this preferred embodiment, constant current stimulation pulses are used. In other words, the total current flowing from all on-high (hi) electrodes is substantially constant for all time slots. For example, if the total pulse current is I, in a time slot where two electrodes are (hi) there will be a current of I/2 flowing from each, in a time slot where three electrodes are (hi) there will be a current of I/3 flowing from each, and so on (assuming the current flows through equal sized electrodes and through pathways with equal resistance). Those knowledgeable in electrical stimulation will understand that a similar technique is applicable using a constant voltage stimulator. The effects of the invention will then be somewhat different but predictable. For instance, the current through a particular pad may not drop when another is added in.

FIG. 6 shows some basic examples of the method according to the preferred invention where electrodes A, B, C and D correspond to electrodes 4a, 4b, 4c and 4d as noted above. In Table 1 electrodes A and D are both on (hi) together for time slot 1 which is indicated with a duration of 100 μs (microseconds). Current passes from these electrodes and sinks in electrode B. During this time slot electrode C is not active. For a given total current the effect of this is to reduce the current density seen under pads A and D but not B.

Next in time slot 2, having a duration of 100 μs, electrode A is still (hi), but electrode D has been shut off. Electrode B still acts as the sink (lo) with electrode C still being off. In this manner, the flow of current between electrodes and therefore through the subject has been altered. Various sequences (for example, those shown in FIG. 6) may be selected to give stimulation of desired muscles or combination of muscles. For example, in accordance with the sequence of Table 4, the glutei muscles are targeted, while in accordance with the sequence of Table 6, the quads receive the most stimulation. The use of such sequences further allows for a greater current, and therefore a more aggressive stimulation to be tolerated by a subject or to target some muscle for other reasons, e.g., therapeutic.

It has further been determined that to maximize energy usage and thus weight loss, the muscles targeted for stimulation are important, as is the position at which the electrode pads are placed on the subject, and as discussed above the effective electrical contact area of the electrode pads. In order to achieve energy usage by the muscles to achieve reasonable weight loss, it is desirable that the large muscles of the legs should be stimulated. The muscles of the thorax and arms may also be stimulating thus adding to the total energy usage, and in turn the amount of calories burnt off. The effective electrical contact area of each electrode will depend on the size of the subject, bigger subjects requiring larger electrical contact area pads, and the muscle groups to be stimulated, as well as the positioning of the electrode pads and possibly other parameters, such as pulse length. If, for example, the pulse signals are being sent from one muscle group in one leg to a similar muscle group in the other leg of the subject, the effective electrical contact area of the electrode pads may be solely determined by the requirement of each muscle group independently. On the other hand, a smaller person may require smaller pads, particularly, for the glutei muscle and muscles of the calf. In certain cases, it may be undesirable to pass the pulse signals from one leg to the other through the pelvis, as this may lead to unacceptable discomfort to the subject. Further, the subject may have other conditions, e.g. being pregnant, that may limit the desirability of passing current through the pelvis.

Any electrical conductor may be used to conduct the current so long as they are pressed very firmly against the skin and they form even contact with the skin. However, in a sweaty environment many hydrogel electrodes may be inappropriate if they absorb water and delaminate. Traditional carbon rubber electrodes similarly are not suited to this form of stimulation, as they are too rigid. In accordance with the invention, the electrodes should not crease as such creases may lead to localized variations in the current density that may causes pain, 'hot spots'. The electrodes therefore need to form a uniform level of contact with the skin. Otherwise there will be variations in current that leads to painful sensations. The electrodes therefore need to conform to the contours of the skin.

The electrodes themselves may be mounted on an inner portion of a garment or banding system, which may be tightened before or after putting on the garment. The tightened position may be secured by Velcro, hoops, zips or other fastening means. The banding/inner garment may come through the outer garment and be secured on the outside.

It has been determined that the application of external pressure to the electrodes greatly enhances the comfort and tolerability of the treatment. The degree of pressure is the most that a subject can tolerate. The pressure forcing the electrodes against the skin is preferably supplied by elements in the garment. An appropriate degree of pressure has been determined to be in the order of 40 mm Hg, as determined by the placing of a small blood pressure cuff under the electrode. The applied pressure must be comfortable for the subject and not be so high as to adversely interfere with blood circulation.

In accordance with the invention, the garment properly places the electrodes on the user in locations as shown in FIGS. 3(a) and 3(b). Thus, by simply putting on the garment and tightening the banding system, the electrodes are assured to be properly located and include a sufficient pressure thereon.

Each electrode is formed with a non-conducive backing positioned between the electrode and the garment. Because the electrode is being used in a sweaty environment, electrolytes in a subject's sweat may provide an electric current to the back of the electrode and to the garment. Thus, if a subject touches the garment near the location of an electrode, a shock may result. Therefore, the non-conductive backing is formed to external beyond the outer edge of the electrode in all directions to insure that no current path is provided from the electrode to the garment. This extension may be fixed to the garment and insures the safety of the subject.

The following examples demonstrate the effectiveness of apparatus 1 constructed in accordance with the invention in achieving cardiovascular training effects in a subject by the use of the shivering-like phenomenon, and for relatively significant calorie usage which may bring about weight loss in the subject.

EXAMPLES

A trial was carried out on nine subjects, namely, subjects aa, bb, ee, ff, hh, jj, kk, pp and rr employing the features of the invention described above. Results from these tests are set out in Tables 1 to 3. In the trial apparatus 1 described with reference to FIGS. 1 to 3b was used. Each subject was subjected to an average of twenty two sessions of muscle stimulation, and each session lasted for a time period of approximately one hour. In general, the pulse signals were applied to the subjects through electrode pads as shown in FIGS. 3a and 3b.

The pulse signal selected throughout the trials was the pulse signal illustrated in FIG. 2(b). The time period between the adjacent current amplitude pulses A and B of the pulse signal was one thirtieth of a second, while the bursts of the respective pulses A and B repeated every one fifth of a second. Thus, the frequency of the bursts of pulses was 5 Hz while the frequency of the pulses was 30 Hz. The current amplitude of the first of the two pulses A and B was approximately half the amplitude of the second pulse, while the amplitude of the second pulse was set in the case of each subject to be as high as the subject could comfortably tolerate, and in all cases was between 80 mA and 200 mA.

Referring now to Table 1 the level of fitness of each subject was determined prior to each subject commencing the trial and at the end of the trial. The fitness level was determined using the Queens College Step Test as described by W. D. McArdle, et al in "Exercise Physiology" fourth edition; by McArdle, Katch and Katch; published by Williams and Wilkins; at page 210, the entire contents of which are incorporated herein by reference. Based on the level of fitness determined by the Queens College Step Test a value of the maximum $VO_2$ for each subject was predicted prior to commencement of the trial. The predicted maximum $VO_2$ value for the subjects aa to rr is set out in the second column of Table 1. The third column of table 1 sets out the maximum $VO_2$ value predicted for each subject at the end of the trial. Columns 4 and 5 of Table 1 set forth the percentage ranking of the subjects before and after the trials, respectively, again based on the Queens College Step Test. The percentage ranking is a way of expressing an individual's fitness in relation to a typical population of 100 Queen's College Students of the same sex as the individual. A percentage ranking of 80 would mean that the individual was fitter than 80% of the students (same sex). Another way to express the percentage ranking is to say that they are in the top 20% of students measured for their fitness levels. The "pre" and "post" columns refer to the measured fitness levels before and after the trials (respectively) with the muscle stimulation method described above. Subject Ee was at the maximum ranking before the trial. Thus, while his fitness level improved, he could not increase his ranking.

Table 2 at Column 2 shows the $VO_2$ consumption of each subject in ml per minute while being electrically stimulated in accordance with the invention, but before being subjected to the trial. Column 3 shows the $VO_2$ consumption of each subject per weight of the subject in kilograms also before commencing the trial. Column 4 in Table 2 shows the energy per minute in kilocalories per minute which could be expended by each subject prior to commencement of the trial. Table 3 shows corresponding results in the corresponding columns for each of the subjects after the trials were completed.

Figures 4A, 4B:
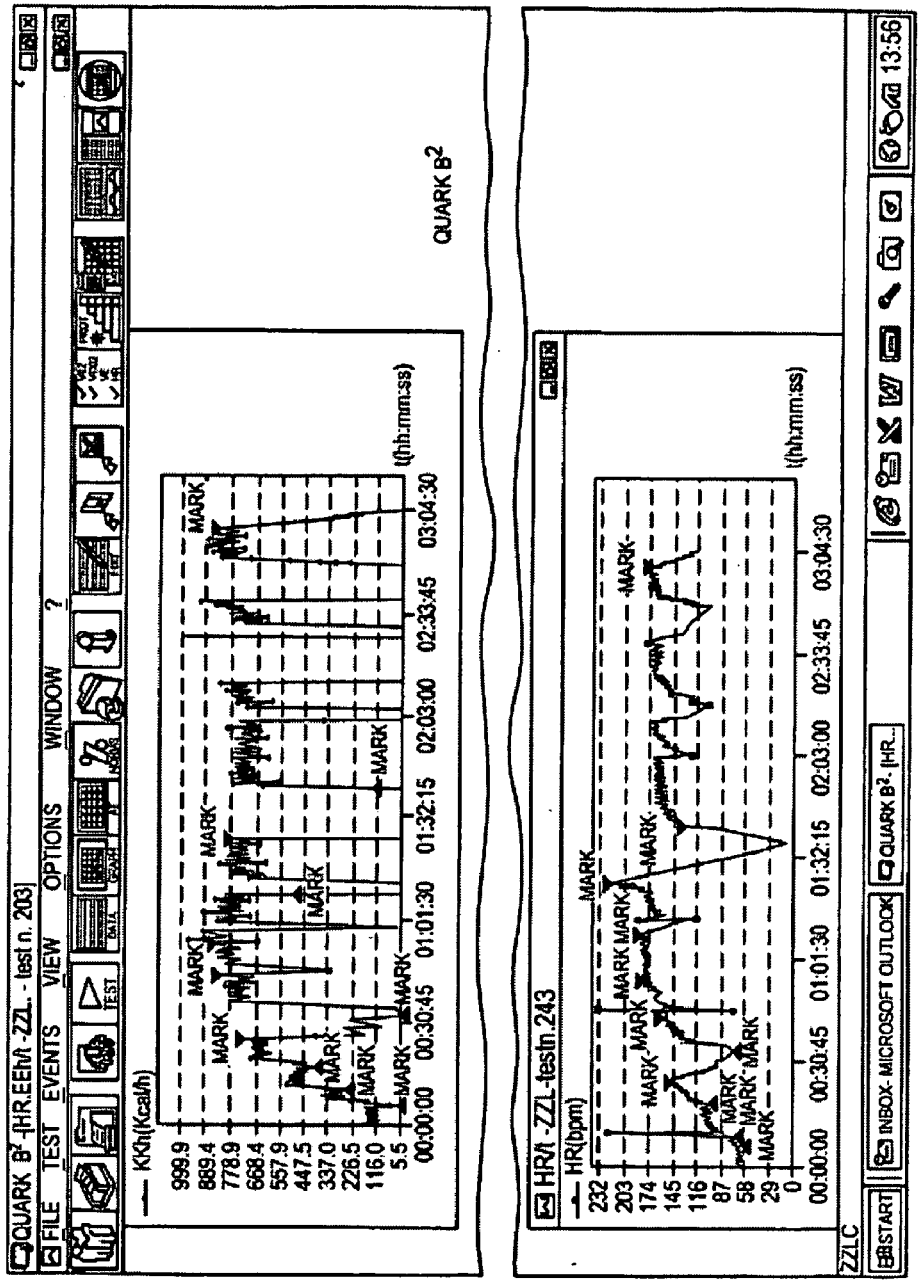
FIGS. 4(a) and 4(b) are graphical representations of parameters of a subject undergoing a trial with the apparatus of FIG. 1.

Graphs 1 and 2 in FIGS. 4a and 4b illustrate respectively the energy consumption and heart rate response of one of the subjects during a three-hour period while undergoing one of the sessions of the trial. The pulse signals applied to the subject were also as described above in this Example, and as illustrated at FIG. 2(b). The subject was sitting with his legs supported. There was no additional voluntary exercise. As is evident from Graph 1 the subject was exercising at a level greater than 600 kcal/hr. This is the equivalent of jogging. From Graph 2 it can be seen that the heart rate of the subject during the session was, in general, in excess of 120 bpm, and this rapid heart rate would be expected to bring about significant training effects on the cardiovascular system.

From the results set forth in Tables 1 to 3 and Graphs 1 and 2 it can be seen that as well as inducing significant cardiovascular training effects in each of the subjects over the twenty two sessions of the trial, significant energy was expended by the subjects in accordance with the shivering phenomenon, that would lead to significant weight loss.

TABLE 1

| Subject | Pre predicted VO$_2$ max | Post predicted VO$_2$ max | Pre % rank | Post % rank |
| --- | --- | --- | --- | --- |
| Aa | 34 | 38.5 | 30 | 90 |
| Bb | 57.6 | 60.9 | 90 | 100 |
| Ee | 60.9 | 68.8 | 100 | 100+ |
| Ff | 45.8 | 44.1 | 50 | 45 |
| Hh | 36.3 | 37.7 | 70 | 85 |
| Jj | 36.3 | 37 | 70 | 80 |
| Kk | 29.6 | 34.8 | 5 | 45 |
| Pp | 40.8 | 42.5 | 25 | 35 |
| Rr | 45.8 | 50.9 | 50 | 75 |
| Mean | 43.0 | 45.3 | 54.4 | 72.8 |
| Stdev | 10.6 | 10.1 | 31.2 | 24.9 | p = 0.24090001 significant
p = 0.0275936 significant

TABLE 2

| Subject | VO$_2$ (ml/min) | VO$_2$/kg | Kcal/min |
| --- | --- | --- | --- |
| Aa | 1019 | 18.54 | 5.1 |
| Bb | 743 | 8.1 | 3.7 |
| Ee | 869 | 13.8 | 4.3 |
| Ff | 902 | 10.4 | 4.5 |
| Hh | 594 | 8.25 | 2.84 |
| Jj | 705 | 11.3 | 3.45 |
| Kk | 997 | 17.5 | 4.9 |
| Pp | 1225 | 11 | 6.1 |
| Rr | 1207 | 16.5 | 6.04 |
| Mean | 917.9 | 12.8 | 4.5 |
| Stdev | 217.3 | 3.9 | 1.1 |
| Range | 594–1225 | 8.1–18.5 | 2.8–6.0 |

TABLE 3

| Subject | VO$_2$ (ml/min) | VO$_2$/kg | Kcal/min |
| --- | --- | --- | --- |
| Aa | 1363 | 24.8 | 6.7 |
| Bb | 2484 | 27.7 | 12.3 |
| Ee | 1861 | 29.5 | 9.25 |
| Ff | 1814 | 20.9 | 9.03 |
| Hh | 1243 | 17.26 | 6.03 |
| Jj | 859 | 13.7 | 4.3 |
| Kk | 1268 | 22.2 | 6.2 |
| Pp | 2448 | 22.45 | 12.1 |
| Rr | 1923 | 26.6 | 9.7 |
| Mean | 1659.9 | 22.8 | 8.4 |
| Stdev | 556.7 | 5.1 | 2.8 |
|  | 859–2484 | 13.7–29.5 | 4.3–12.3 |

Figure 5A:
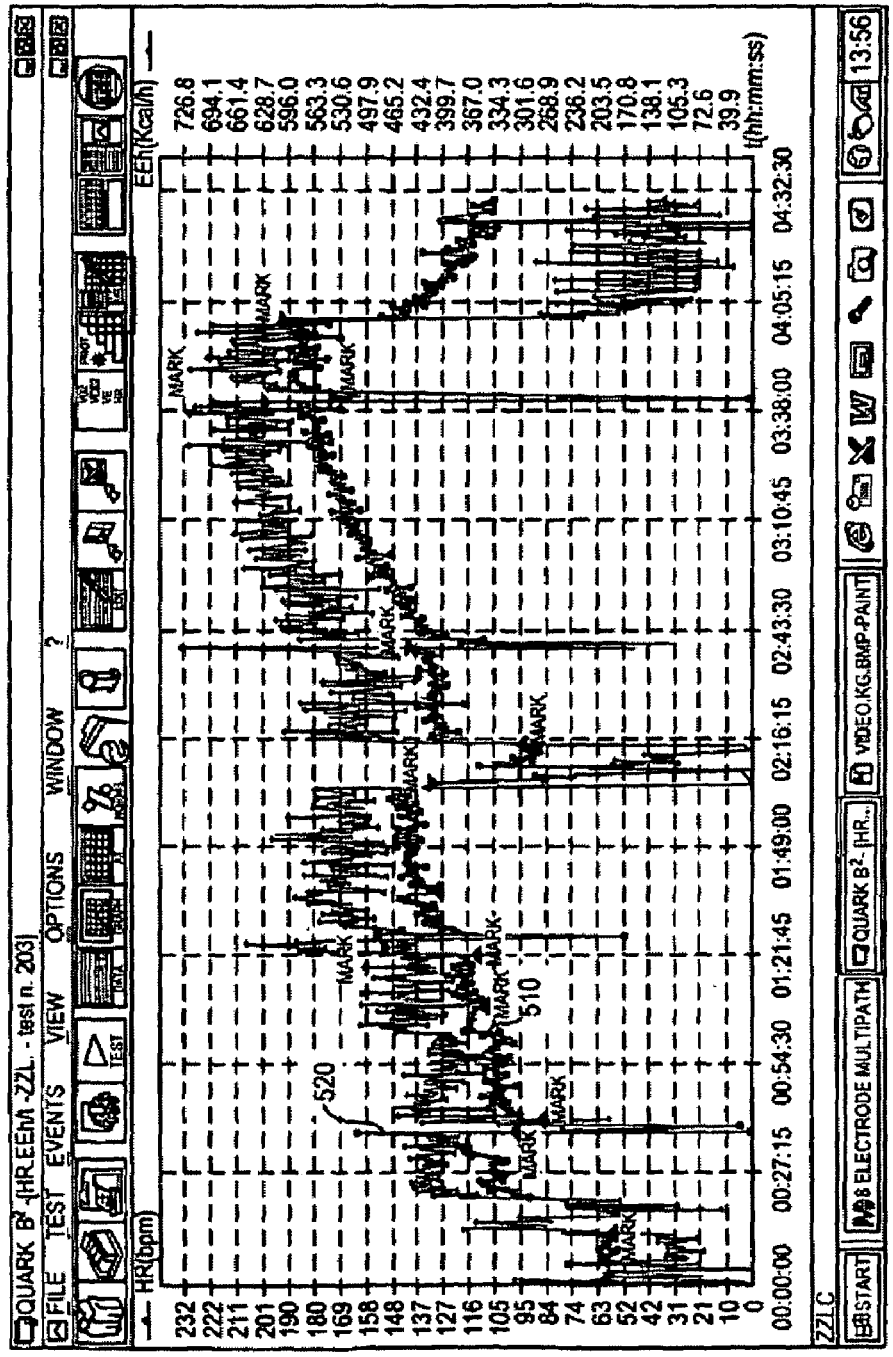
FIG. 5(a) is a graph depicting a heart rate response and energy consumption during use of the apparatus of FIG. 1.
Figure 5B:
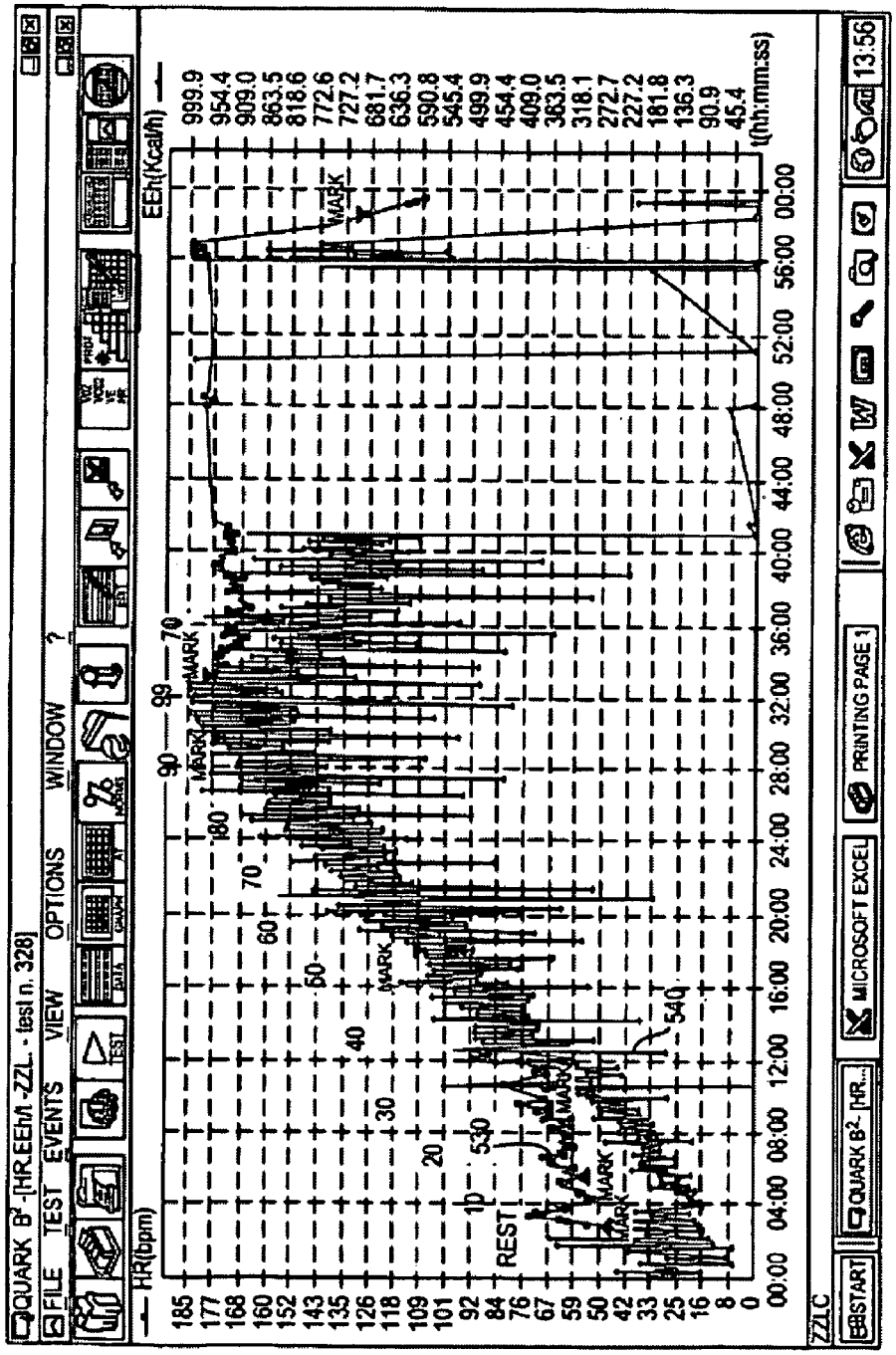
FIG. 5(b) is a graph depicting a dose-response graph during use of the apparatus of FIG. 1.

Referring next to FIGS. 5a and 5b, a second example of the use of the apparatus in accordance with the invention is shown. FIG. 5a depicts a heart rate response and energy consumption response during a 4 hour training session. This time was selected because the typical American watches about 4 hours of TV daily. The apparatus was set to an intensity level at which the subject could comfortably use the apparatus for 4 hours. Track 510 represents the heart rate response of the subject while track 520 represents the caloric consumption of the subject during the trial. The marks on the graph indicate events such as increasing the intensity. The cumulative energy consumption for the 4-hour trial is over 2,000 kcal. For an individual of approximately the same weight as that of the subject, this is approximately equal to running twenty miles in 4 hours, all while watching TV. During this trial the subject sweated about 4 pints.

Referring next to FIG. 5b, a dose-response graph is shown. Trace 530 again depicts the heart rate of the subject while trace 540 depicts energy consumption. The marks refer to increments of ten on the intensity of the electrical stimulation, as shown numerically on the graph. As is evident from the graph, there is more or less a linear relationship between intensity of electrical stimulation and energy consumption. At the maximum intensity (99) the subject was exercising at a rate of about 900 kcal per hour or 15 kcal per minute or oxygen consumption of 40 ml per kilogram bodyweight per minute. This is the equivalent of very vigorous voluntary exercise.

A number of safety features may also be incorporated into the apparatus in accordance with the invention in order to prevent excessive muscle stimulation, and in particular for avoiding overstressing of the subject. Because the apparatus exercises the cardiovascular system it has the potential to overstrain the system, which could have serious and indeed fatal results on subjects with heart disease or other ailments. Accordingly, to overcome this potential problem a heart rate monitor is provided from monitoring the heart rate of the subject. The signal generator is responsive to the heart rate monitor. A microprocessor is also provided that allows the apparatus to be programmed so that the maximum allowable heart rate can be set depending on the subject, his or her heart condition, age and other relevant parameters. The microprocessor reads signals from the heart rate monitor, and in turn controls the signal generator in response thereto. Additionally, the microprocessor is programmed to control the length of each session, and the frequency with which a subject may be the subject of a session.

Other monitors as well as or instead of a heart rate monitor may be provided as desired. For example, a blood pressure (BP) monitor, a pulse oximeter, a glucose monitor, a respiratory monitor, metabolic gas analysis, EEG, or an EMG monitor may be employed. The heart rate monitor may be provided as an ECG monitor or any other suitable monitor. The apparatus may be responsive to changes in the ECG pattern, for example, ST segment depression or arrhythmias in order to control the application of the various electrical pulses. Indeed, in the case of the monitor being provided by an ECG or an EMG, in certain cases, the electrode pads that are used for stimulating the muscles may also be used for picking up the ECG or EMG signals. The monitor or monitors may be a discrete unit that is coupled to the apparatus via a wire, or may communicate with the apparatus through IRDA radio frequency, using bluetooth technology or the like. A further monitor, such as an accelerometer may be employed. Such a meter is positioned adjacent a muscle of the subject that is being stimulated. This meter then tracks the magnitude of the shivers generated in the muscle. If this magnitude exceeds a predetermined level, the apparatus is notified and may be adjusted or shut off.

It has also been determined that fatigued muscles give a different EMG signal as compared with non-fatigued muscles. This is true both in response to a pulse train which comprises single pulses at the appropriate 4 Hz to 8 Hz or bursts of pulses at higher frequencies whereby the frequency of the bursts is in the order of 4 Hz to 8 Hz, as well as in the recovery/relaxation phases of the stimulation session. Thus, the microprocessor may be programmed in order to reduce the amplitude or amplitudes of the pulse signal or terminate a treatment session in the event of the EMG response showing signs of muscle fatigue. By way of example, if the magnitude of the EMG response to a given test signal sent out on a regular basis dips below, for example, 70% of the original response the unit may automatically reduce the amplitude or amplitudes of the pulse signal.

Those with peripheral vascular disease may not experience the normal warning signs during use of the apparatus, and accordingly, a pulse oximeter placed, for example, on a toe may be provided for terminating a treatment session if the oxygen hemoglobin saturation falls below, for example, 90%. Similar comments would apply should the monitoring means include a blood flow meter or a glucometer.

In accordance with the invention, pulse signals may be sent from one of the electrode pads to another of the electrode pads of a pair, or even to another set of electrode pads for determining the bioimpedence of the body. As the position of the electrodes while the system is in use will remain substantially constant during each session, by monitoring the body bioimpedence, the subject may track his or her individual progress, thereby motivating the subject to persist in the training regimen.

The control unit may also monitor the likely calorie expenditure, based on a table of weight, time, heart rate and intensity of usage, (or it could be individually calibrated). Usage time may then be set at a calorie consumption level, (e.g. an American Heart Association recommended level of 300 kcal). The unit would indicate when this target is reached.

Additionally, a monitoring means for determining if a subject collapses during a session may be provided. In such a case the microprocessor would immediately switch off the apparatus. Such a monitoring means may, for example, be provided by a tilt switch that would be placed on the subject which would trip out on the subject collapsing, or may comprise a "dead man's switch". In this particular case the microprocessor may be programmed that upon receipt of such a signal, the microprocessor would communicate with the outside world for summoning assistance to the subject. Such communication may be through a telecommunications network, a radio transmission, or indeed by an alarm that would summon assistance from an adjacent room or the like.

Additionally, the microprocessor may be programmed to personalize the apparatus to the needs of one or more subjects who will be using the apparatus, and monitor and store results of each treatment session so that the progress of each subject can be individually monitored. Further, long term program tracking and incentive features may also be included. Various statistical data for each subject, or groups of subjects may be calculated and displayed based upon the stored data.

It has also been determined that as well as being suitable for facilitating weight loss and for increasing exercise tolerance of the subject, the apparatus may be used in the treatment of any medical condition where vigorous exercise of large muscle groups would be beneficial, e.g. the treatment of hypothermia.

Additionally, it has been determined that subjects are able to sleep quite comfortably with this type of muscle stimulation if it is used at submaximal levels. This method allows the muscles to contract very comfortably and thus not interfere with sleep when used at submaximal levels. In one embodiment of the invention the apparatus is programmed not to give any palpable pulses for a defined period of time, say two hours. This phase may also be terminated by changes in the heart rate or EEG that indicate a sleep depth, or a likelihood of waking up. This allows the subject to fall asleep as usual. During the next phase after sleep has commenced the intensity of the pulses gradually increases over a period of time, for example, ten minutes. This avoids a sudden change that may awaken the subject. During the next phase the apparatus is operated at a predetermined current amplitude level, usually in the range of 20% of maximal. This phase may last until the subject wakes up, or it may last for a predetermined time, say four hours. In one embodiment of the invention the apparatus incorporates an alarm clock. The prolonged usage periods allow for significant amounts of energy to be expended during the night.

In one embodiment of the invention this nocturnal stimulation is linked to a heating or cooling device. To fall into a deep sleep an individual needs to be warm. However, if too much bed clothing is used a subject may be uncomfortably warm during the stimulation as heat is generated. To overcome this problem the apparatus functions in conjunction with an electric heater/blanket and/or a fan. During the periods when the energy consumption is low the electric blanket is on or at a higher level. Conversely when the energy consumption is high a fan or other cooling device works at a higher level.

In addition to calorie burning and training the inventors have determined a number of other benefits from the use of the apparatus and method in accordance with the invention. Most of the positive effects of exercise may be induced with electrical stimulation in accordance with the invention, and indeed, in many cases there is an advantage in using electrical stimulation as compared with conventional exercise, for instance subjects with diminished consciousness, e.g. a coma Another example is groups of people who are unable/have a diminished capacity to exercise, for example, patients post-stroke, arthritis sufferers, or spinal cord injured patients whose life expectancy is thought to be curtailed by inactivity. Also, such activity may assist in reducing the effects of these various problems. A further example is groups of people who may benefit from exercise that generates an increased depth or rate of breathing.

A patient suffering from severe hypothermia could obviously potentially benefit. Also, other times when increased metabolic rate would be of benefit, potentially some hyperglycemic states, or the need to increase excretion of volatile substances, such as alcohol or anaesthetic gases may employ the invention.

In accordance with the invention, post-exercise euphoria may be experienced. Exercise is known to have positive psychological effects. For instance it can stave off depression. Of course, most depressed people do not exercise, (if they had that level of self-motivation they might not be depressed). However, the apparatus and method in accordance with the invention could be applied to them in their hospital beds helping to lift their depression. Further, in certain conditions, such as cardiac failure and chronic obstructive airwave disease patients, a greater and more controlled level of exercise may be available.

Advantageously, it has also been determined that equivalent energy consumption using this technique (as compared with regular exercise) seems to be associated with less side effects of exercise. In particular, post exercise stiffness seems to be markedly lessened. Furthermore, as there is less joint movement and less weight bearing there is less joint damage. The invention may also provide a good treatment for osteoporosis, or at least a way for those stricken with osteoporosis to exercise without putting themselves in danger. Another example would be patients with angina. These patients may be able to exercise for longer and at a higher level of exertion before they experience any chest pain.

It will thus be seen that the objects set forth above, among those made apparent from the preceding description, are efficiently attained and, since certain changes may be made in the above construction(s) without departing from the spirit and scope of the invention, it is intended that all matter contained in the above description or shown in the accompanying drawing(s) shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed:

1. A method for stimulating a plurality of muscles of a subject, comprising the steps of:
   generating an electrical pulse signal in accordance with one or more predetermined parameters for stimulating the muscles by inducing vibrations therein;
   applying the signal to nerves associated with the muscles of the subject to be stimulated;
   selecting the predetermined parameters of the electrical pulse signal to cause a predetermined cardiac output of at least 50% of the maximum cardiac output of the subject;
   monitoring the cardiovascular response of the subject; and
   controlling said signal generator based upon the cardiovascular response.

2. The method of claim 1, wherein the electrical pulse signal induces vibrations in the muscle within a range of 3 Hz to 12 Hz.

3. The method of claim 2, wherein the electrical pulse signal for induces vibrations in the muscle within a range of 4 Hz to 8 Hz.

4. The method of claim 1, wherein said predetermined cardiac output burns calories in the muscles of the subject without performing any external work by the subject.

5. The method of claim 1, wherein a cardiovascular response is generated in response to the induced vibrations.

6. The method of claim 5, wherein said cardiovascular response is greater than 50% maximum cardiac output.

7. The method of claim 5, wherein said cardiovascular response is greater than 60%-70% maximum cardiac output.

8. The method of claim 1, further comprising the step of selecting the predetermined parameters of the electrical pulse signal generated by the signal generator to minimize discomfort to the subject.

9. The method of claim 1, wherein the electrical pulse signal comprises a plurality of single pulses at a frequency for inducing the vibrations in the muscles of the subject within a predetermined frequency range.

10. The method of claim 9, wherein said frequency range of the vibrations induced in the muscles of the subject is from 3 Hz to 12 Hz.

11. The method of claim 1, wherein a charge-per-pulse of one or more pulses of the electrical pulse signal, and the electrode apparatus for applying the pulse signal to the subject co-operate with each other to maintain the charge-per-pulse per unit area of the applied electrical pulse signal at or below 16 nC/mm$^2$ in the subject.

12. The method of claim 11, wherein the current density is maintained at or below 0.1 mA/mm$^2$.

13. The method of claim 1, wherein a maximum charge-per-pulse of the electrical pulse signal exceeds approximately 60 micro-Coulombs.

14. The method of claim 1, wherein the pulse signal is applied to the subject by an electrode.

15. The method of claim 1, wherein the pulse signal is applied to the subject by a plurality of electrodes.

16. The method of claim 15, wherein the effective electrically conductive contact area of at least one electrode is not less than 7,500 mm$^2$.

17. The method of claim 16, wherein the effective electrically conductive contact area of at least one electrode is not less than 10,000 mm$^2$.

18. The method of claim 17, wherein the effective electrically conductive contact area of at least one electrode is not less than 15,000 mm$^2$.

19. The method of claim 15, wherein at least one of the electrodes has an effective electrical contact area such that the length of the effective electrical contact area is substantially similar to the width of the muscle to be stimulated.

20. The method of claim 19, wherein when it is desired to stimulate a quadricep or hamstring muscle group in a male of average size, the length of the effective electrical contact area of the relevant electrode is at least 140 mm.

21. The method of claim 20, wherein when it is desired to stimulate a quadricep or hamstring muscle group in a male of average size, the length of the effective electrical contact area of the relevant electrode is at least 190 mm.

22. The method of claim 15, wherein at least one of the electrodes has an effective electrical contact area such that a maximum charge may be applied to the muscles of the subject while minimizing discomfort to the subject.

23. A method for stimulating a muscle of a subject, comprising the steps of:
   generating an electrical pulse signal in accordance with one or more predetermined parameters for stimulating the muscle by inducing vibrations therein;
   applying the signal to nerves associated with the muscle of the subject to be stimulated for stimulating the muscle;
   selecting the predetermined parameters of the electrical pulse signal to cause a predetermined cardiac output of at least 50% of the maximum cardiac output of the subject;
   monitoring the cardiovascular response of the subject; and
   controlling said signal based upon the cardiovascular response;
   wherein the pulse signal comprises a plurality of single pulses, and the frequency of the respective pulses lies in the range 4 Hz to 12 Hz.

24. The method of claim 23, wherein the pulse signal comprises a plurality of single pulses, and the frequency of the respective pulses lies in the range of 4 Hz to 8 Hz.

25. The method of claim 23, wherein at least two of said plurality of single pulses are of different amplitudes.

26. A method for stimulating a muscle of a subject, comprising the steps of:
   generating an electrical pulse signal;
   applying the signal to the muscle of a subject to induce vibrations therein; and
   selecting one or more predetermined parameters of the electrical pulse signal to maximize the bulk of the muscle being subjected to the vibrations to induce cardiovascular training effects in the subject and cause a predetermined cardiac output of at least 50% of the maximum cardiac output of the subject;
   monitoring the cardiovascular response of the subject; and
   controlling said signal based upon the cardiovascular response.

27. The method of claim 26, wherein said cardiovascular training induces relatively significant calorie usage in the subject.

28. The method of claim 26, wherein said cardiovascular training induces one or more benefits of aerobic exercise in the subject.

29. A method for stimulating a muscle of a subject, comprising the steps of:

generating an electrical pulse signal in accordance with one more predetermined parameters for stimulating the muscle by inducing vibrations therein;

applying the signal to nerves associated with the muscle of the subject to be stimulated for stimulating the muscle;

monitoring one or more physiological parameters of a subject;

controlling said signal generator based upon an output of said monitoring; and selecting the predetermined parameters of the electrical pulse signal to induce the predetermined cardiac output of at least 50% of the maximum cardiac output of the subject.

30. The method of claim 29, wherein said monitoring is performed by a heart rate monitor, and said predetermined parameters of said electrical pulse are varied based upon a heart rate of said subject.

31. A method of stimulating muscles in a subject, comprising:

generating an electrical pulse signal;

applying the signal to nerves associated with muscles of the subject to be stimulated;

inducing muscle vibrations in a predetermined frequency range by selecting parameters of the electrical pulse signal;

controlling the induced muscle vibrations to cause a cardiac output of at least 50% of the maximum cardiac output of the subject.

32. The method of stimulating muscles according to claim 31, wherein the predetermined frequency range is from 3 Hertz to 12 Hertz.

* * * * *